United States Patent
Bagan

(10) Patent No.: US 7,988,627 B2
(45) Date of Patent: *Aug. 2, 2011

(54) BIOMETRIC NETWORK EXCHANGE SYSTEM

(76) Inventor: Kenneth J. Bagan, Highland Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/550,663

(22) Filed: Oct. 18, 2006

(65) Prior Publication Data

US 2008/0114213 A1    May 15, 2008

(51) Int. Cl.
*A61B 5/00* (2006.01)
*G06Q 50/00* (2006.01)
*H04W 4/16* (2009.01)

(52) U.S. Cl. ............................ 600/300; 705/2; 455/466
(58) Field of Classification Search .................. None
See application file for complete search history.

(56) References Cited

U.S. PATENT DOCUMENTS

| | | | |
|---|---|---|---|
| 6,403,897 B1* | 6/2002 | Bluth et al. | 600/301 |
| 6,478,736 B1* | 11/2002 | Mault | 600/300 |
| 6,579,231 B1* | 6/2003 | Phipps | 600/300 |
| 6,595,929 B2* | 7/2003 | Stivoric et al. | 600/549 |
| 6,692,436 B1* | 2/2004 | Bluth et al. | 600/300 |
| 2004/0260577 A1 | 12/2004 | Dahlin et al. | |
| 2005/0192841 A1 | 9/2005 | Hays et al. | |

* cited by examiner

*Primary Examiner* — Eric F Winakur
*Assistant Examiner* — Bobby Soriano
(74) *Attorney, Agent, or Firm* — Leydig, Voit & Mayer, Ltd.

(57) ABSTRACT

A biometric measurement device and communications infrastructure implements a system of information exchange and usage. In an embodiment of the invention, a kiosk user's cell phone is used to wirelessly connect via the machine to a call center, doctor, or emergency center. In addition, the kiosk may automatically and wirelessly connect the user's cell phone through the kiosk to a call center representative or emergency service. The kiosk is able to collect and transmit user data, such as for promotional or advertising purposes in a further example.

4 Claims, 5 Drawing Sheets

US 7,988,627 B2

BIOMETRIC NETWORK EXCHANGE SYSTEM

BACKGROUND OF THE INVENTION

A number of companies have successfully provided public kiosk blood pressure machines for a number of years. These devices allow users to obtain a reading of their blood pressure during a break while shopping etc. Users are concerned about their blood pressure primarily for health reasons, and are typically unable to otherwise obtain a reading without visiting a doctor or other health practitioner. The blood pressure machines are thus very popular and millions of people have availed themselves of the services provided by such machines. Blood pressure kiosks can be used for advertising purposes to generate an additional revenue stream such as by having large consumer product companies advertise. However, such known systems are less than ideal for a number of reasons that will become apparent hereinafter.

The present inventor has been instrumental in the biometrics area for almost 30 years. In that time, he has created new and useful systems and advanced the state of the art. In one example he has created a system of blood pressure kiosks in university settings by deploying a number of LifeClinic® model 9000 units to colleges free of charge. Although the number of units deployed at that time was small, the exercise did show that the machines were potentially popular with university students and staff. However, that implementation did not employ or benefit from the structures, methods, and techniques that are described herein for improving the state of the art.

BRIEF SUMMARY OF THE INVENTION

Embodiments of the invention pertain to biometric measurement devices coupled with a communications infrastructure to implement a system of information exchange and usage. Although the examples herein pertain primarily to the biometric parameters of weight, blood pressure, pulse rate, body fat and blood oxygen (via oximeter), it will be appreciated by those of skill in the art that any suitable biometric measurement device may be used additionally or alternatively.

In an embodiment of the invention, a LifeClinic® model LC500 unit is used to implement the intercommunicating health kiosk, but any machine with similar functionality may be used instead. The tests that are currently available on this machine are weight, blood pressure, pulse rate, body fat and blood oxygen. In addition, diabetics can download a history of readings from certain glucose meters into an internet-connected kiosk. At a later time, the user can retrieve the readings on a public (i.e., LifeClinic®) website and/or dedicated website. In addition, users of the internet-connected machines may email their history of readings to their doctors in preparation for an upcoming physical exam etc.

In another embodiment of the invention, an internet-connected kiosk user can call a call center to get answers to questions about their readings and/or about one or more drugs. In an embodiment of the invention, a kiosk user's cell phone is used to wirelessly connect via the machine to a call center, doctor, or emergency center. This alleviates concerns regarding the sanitation of a dedicated phone attached to the kiosk. Thus, the user can talk to the device sponsor's call center for any information he or she needs using their own cell phone.

Very high readings cause the kiosk to connect the user's cell phone to the kiosk (e.g., via Bluetooth) and then through to a call center representative for counseling. For dangerous readings, the kiosk may instead connect the user's cell phone to an emergency service representative. When communicating with the user's cell phone, the kiosk may target devices within a small enough radius to likely include the cell phone, e.g., 2 or 3 feet.

In an embodiment of the invention, a camera is built into the kiosk pod so that the call center representative can see the customer during a conversation. In addition, in an embodiment of the invention, the kiosk incorporates a screen to allow the user to see the call center representative, if so desired. There are also other features according to various embodiments of the invention that will be discussed in the examples of the various health connect networks discussed below.

DETAILED DESCRIPTION OF THE INVENTION

As discussed above, embodiments of the invention pertain to biometric measurement devices coupled to a wide area network such as the Internet. The link to the network may be implemented by way of wired or wireless connections or a combination thereof, and while high speed connections such as DSL are preferred, slower connections may instead be used.

Figure 1:
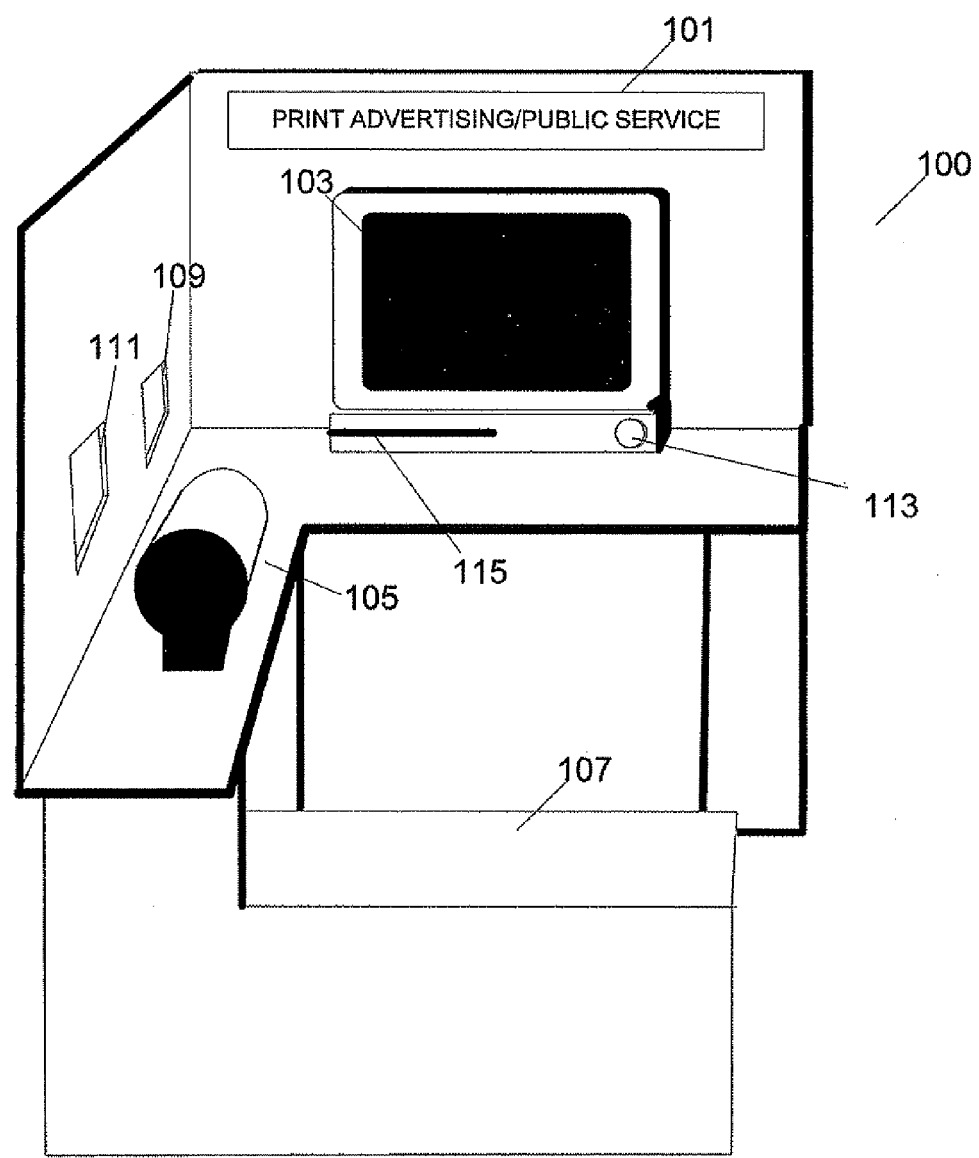
FIG. 1 is a simplified illustration of a kiosk for use within an embodiment of the invention.

FIG. 1 is a simplified illustration of a kiosk for use within an embodiment of the invention. The kiosk 100 includes a seat 107 for the user of the machine as well as a cuff 105 for obtaining a nonintrusive blood pressure reading from the user. The seat 107 may include a scale for determining the user's weight. In addition to the foregoing elements, the kiosk 100 also includes a number of display elements including a screen 103 for displaying information to the user electronically, as well as a print ad area 101 for displaying entertaining or informative print material such as advertising material or public service information.

For use in a further embodiment of the invention, the kiosk 100 may also contain built-in receptacles 109, 111 for the deposit of materials from the user. In an embodiment of the invention, the receptacles 109, 111 are used to receive donated items such as money, used hearing aids, old glasses, canned goods, and the like. In this embodiment of the invention, the kiosk 100 also preferably includes containers associated with the receptacles 109, 111 to hold the donated items. The receptacles 109, 111 are secured in an embodiment of the invention such that items may be dropped into the receptacles 109, 111 but may not be taken out by a user without a key, code etc. to unlock the associated containers.

The kiosk 100 may also comprise a camera (not shown) for capturing an image of the user (video or still), such as for use during a video call with a call center or for security purposes. Security can be by way of a simple image obtained by the camera, or by way of retina scanning or fingerprint scanning to verify the identity of the person being tested.

When using the kiosk, a user sits at the seat 107 and places their arm into the cuff 105. After activating the unit such as via a button 113, the cuff inflates and a reading is taken over the course of a short period of time. While awaiting their reading, the user may read the printed material in area 101 and/or view the material displayed on the screen 103. In an embodiment of the invention, the kiosk 100 includes a switch activated by a user sitting on the seat. In this embodiment, closing of the switch may initiate the presentation of menus etc. to the user. Moreover, opening of the switch when the user stands clears the user's data from the screen in a further embodiment of the invention.

In an embodiment of the invention, the kiosk 100 further comprises a card reader 115 such as an optical or magnetic reader. The reader 115 allows the user to slide a card and convey information to the kiosk 100. In a further embodiment of the invention, the user may input data to the kiosk 100 via a keyboard (not shown) or a touch screen interface such as via display 103.

Figure 2:
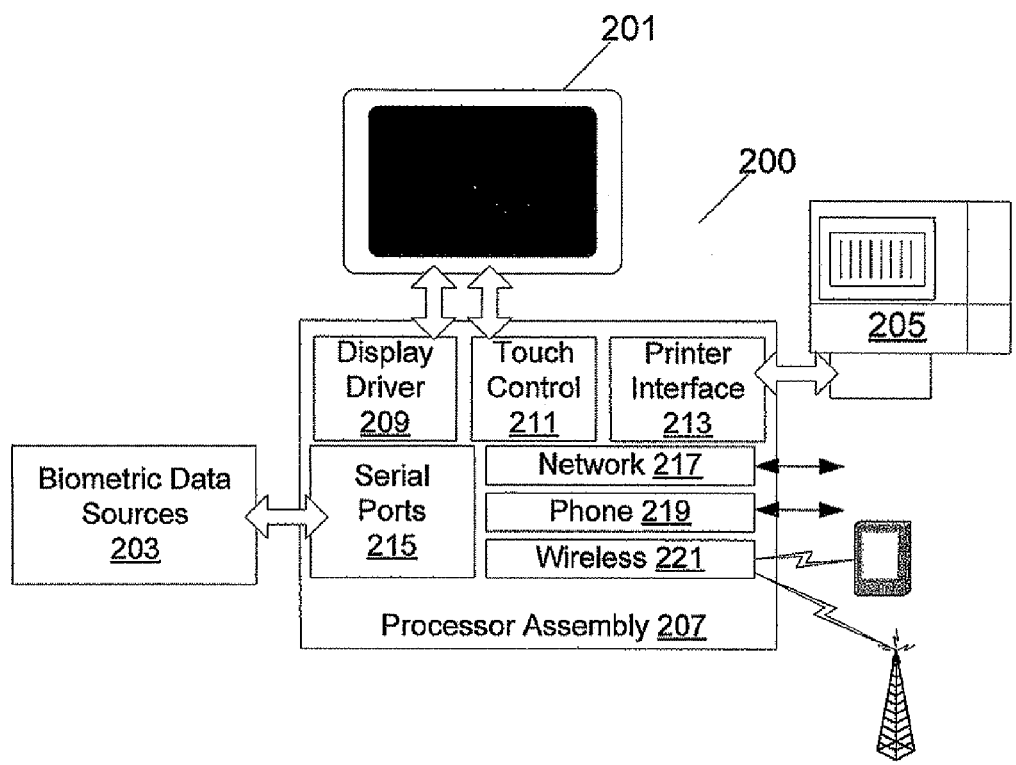
FIG. 2 is a schematic diagram of a kiosk usable within embodiments of the invention.

In an embodiment of the invention, the kiosk 110 is able to stimulate multiple senses in addition to sight and hearing. For example, the user's sense of smell can be used in a restaurant and/or health food store kiosk to promote bakery goods, etc. In addition, when an advertisement is playing on the display 103, the kiosk 100 may provide a tactile sensation such as a movement or vibration of the seat. With respect to taste, the kiosk may provide free or low-priced samples of edible products in much the same manner that a vending machine supplies products. It will be appreciated that the kiosk requires additional components to serve the senses of touch, taste, and smell. For example, movement of the seat would employ an actuator beneath the seat linked to a controller in the processor assembly, discussed below. Similarly, the use of scent technology would require appropriate scent distribution facilities, again preferably linked to the processor assembly As discussed above, the kiosk 100 also comprises a link to a network. This and other detailed aspects of the device are illustrated schematically in FIG. 2. In particular, FIG. 2 is a schematic diagram of a kiosk usable within embodiments of the invention. The kiosk 200 comprises biometric data sources 203 (e.g., blood pressure cuff and associated electronics, scale and associated electronics, etc.), a display 201 and a printer 205.

These elements 201, 203, 205 are linked, typically by wired connections, to a processor assembly 207. The display 201 interfaces with the processor assembly 207 via a display driver 209 and a touch control module 211. The touch control module 211 receives and processes touch screen inputs from the display 201. The biometric data sources 203 interfaces with the processor assembly 207 via serial ports 215. Finally, the printer 205 interfaces with the processor assembly 207 via a printer interface 213.

The processor assembly 207 also comprises data links to external data sinks/sources. For example, in the illustrated embodiment of the invention, the processor assembly 207 comprises a network communication module 217, a phone communication module 219, and a wireless communication module 221. As will be discussed in greater detail below, the wireless communication module 221 allows connectivity to a cellular network and/or to local wireless devices (e.g., a PDA or cell phone) via a short range protocol such as Bluetooth. The network communication module 217 provides connectivity (wired or wireless) to one or more networks such as a local area network (LAN) and the Internet.

Figure 3:
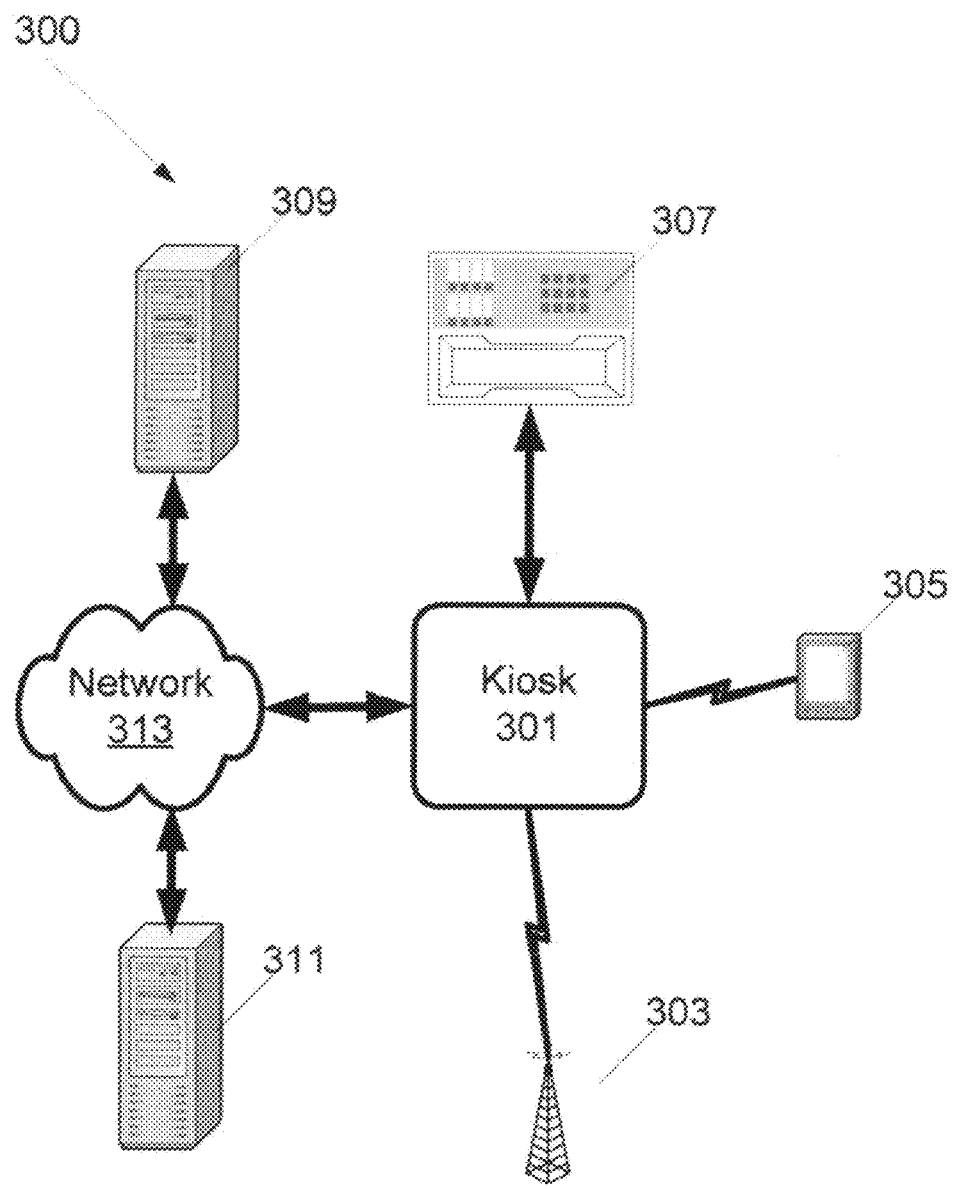
FIG. 3 is a schematic diagram of the network operating environment 300 of the kiosk within an embodiment of the invention.

FIG. 3 is a schematic diagram of the network operating environment 300 of the kiosk within an embodiment of the invention. As illustrated, the kiosk 301 is communicably linked to a phone system 307, such as via ordinary phone lines. The kiosk 301 is also linked wirelessly to a cellular network 303 and a local wireless device 305, e.g., a Bluetooth equipped device. The local wireless link allows the user to use their own phone to communicate to or from the kiosk as well as to place a call through the kiosk to a customer service representative or advisor.

Finally, the kiosk 301 is linked via a network 313 to a number of networked data sources/sinks, e.g., servers 309, 311. In an embodiment of the invention, server 309 is an operator server of the company or other entity responsible for the kiosk. For example, LifeClinic® is the operator of kiosks that are placed in thousands of locations across the country. In this embodiment of the invention, the other server 311 is associated with a sponsor or other entity interested in receiving data from the kiosks as will be discussed in greater detail below.

The data transferred over the network links to/from one or both of servers 309, 311 to/from the kiosk 100 includes in an embodiment of the invention any or all of the communication indicated herein, including but not requiring: waiver, identity, readings, demographics and other data from the kiosk 100; instructions, video, communications, prior readings, and advertisements from the server(s) 309, 311.

Kiosks of the type described above can be used for a number of activities and interchanges that provide value to both the community and the sponsor or business supporting the machine. In a first example, the kiosk can be used to provide entertainment such as via television or video. The entertainment content may be customized for the sponsor, e.g., a department store, or may be publicly available entertainment. In this embodiment of the invention, the entertainment provides a draw for customers who may not be interested in shopping or may be tired. For examples, men accompanying women in a predominantly female-oriented store may prefer to rest at the kiosk. In an embodiment of the invention wherein the user identifies themselves by swiping a loyalty card, credit card, etc., the system can provide customized services. For example, if the system is able to access recent purchase history, it will supply appropriate coupons via the attached printer to encourage the user to avail themselves of the goods or services of the sponsor. More generally, a credit card or gift card's magnetic stripe may supply identity information both for customization of services and to track a user's biometric readings.

In this embodiment of the invention, the user may be presented with menu options to choose an activity. For example, a user may be asked to choose from a health test, health information, sports scores, sports highlights, interviews, news, current affairs, exercise tips, etc. In another example of the invention, the kiosk provides one or more maps or informational items related to the store hosting the kiosk. Advertisements are run during these services and can be customized if the customer uses a personalized gift card or credit card.

In a second example, the kiosk can be used to provide an emergency alert to the user. In particular, certain biometric measurements can convey information sufficient to indicate whether the user may in or about to enter a dangerous state. For example, blood pressure readings can indicate that a person is having, or is close to having, a stroke. In this case, the kiosk will call the user's cell phone automatically and connect the user to an emergency service, so that a paramedic may further diagnose and advise the user. This especially useful for older users who may not be able to dial a help number.

In a third example, the kiosk can be used to provide public safety announcements such as Amber Alerts and All Points Bulletins. Because the operator server 109 is preferably linked to many kiosks, the system is able to provide a widespread warning regarding unfolding events. Warnings can also be targeted to specific regions. Examples of targeted warnings include tornado, storm, and nuclear warnings. In addition to providing a warning, the kiosk may also provide instructions for responding to the emergency.

In a fourth example, the kiosk can be used to provide public service ads. These may be placed where appropriate during the testing cycle. For example, during weight tests or body fat tests, the kiosk may present a warning that 20% of university students have an eating disorder, and advise the user to lose weight only in consultation with a healthcare professional.

The way in which the kiosk may be used depends to some extent on the environment in which it is used. The following examples tie certain functionalities to certain environment, although it will be appreciated that these are just examples, and the attributes discussed below may be applied to any appropriate environment.

One exemplary environment is a mall network, i.e., a number of kiosks in one or more malls linked via the Internet or other network to operator and/or sponsor servers. In the mall network, the sponsor (e.g., the mall operator/owner) may place static advertisements on the kiosks in the traditional manner. However, in addition, the mall kiosk network provides marketing information to the owner/operator for their own use or for trade or sale. For example, a user may apply for and acquire a health information card, e.g., a co-branded magnetic stripe card promoted by the owner/operator and a credit card company or other enterprise.

At the time that the user applies for the card, they preferably supply their name and address and may also be asked to respond to other questions that are of significance with respect to marketing. At that time as well, the customer also preferably signs a waiver at the information desk whereby they agree that their name and/or other information can be used for promotional and/or advertising purposes by the owner operator, etc. The user is then given a bar coded or magnetic coded loyalty card that encodes or is linked to his or her identification, address, etc.

When the user subsequently uses the kiosk at the mall, they are asked to put their bar code by the bar code reader. This allows the kiosk to retrievably store the user's readings and also to access the user's name, address, etc. for promotional purposes. A waiver may appear on the display at this time as well.

In an embodiment of the invention, user names and data are collected and transmitted to a server such as a sponsor server or operator server. This transmission may be ongoing or may be hatched on a daily basis, weekly basis, etc. The recipient will thus accumulate many thousands of names over the course of a year. The collected names can be used by the recipient for advertising or promotional purposes or may be sold to marketing companies to subsidize the provision of the kiosks and the health benefits that they provide to the public.

In addition, in an embodiment of the invention, advertisements can be downloaded by the owner/operator to be played during the biometric tests. This provides an additional revenue stream. For example, the advertiser will preferably compensate the owner/operator for displaying the advertisement. In addition, mall tenants may be given or leased advertising time to create goodwill with the mall tenants.

In addition, the data provided by a gift card or a credit card may also provide a buying history of the user to allow customization of messages and advertising. For example, the kiosk could recommend stores similar to those that the user had patronized recently. Additionally, as discussed above, the kiosk may provide customized coupons based on the user's demographic data (race, class, income, age, ethnic origin, language, location, dwelling type, family size/type, gender, occupation, etc.) or buying history.

Another exemplary environment is a university network, i.e., a number of kiosks in one or more universities linked via the Internet or other network to operator and/or sponsor servers. One or more universities may additionally be divided into subnets such as a student union network, a recreation center network and a student health center network. For example, the student union network may be attractive to active sponsors such as automobile companies, to provide the sponsor's advertisements via the display of the kiosk. Similarly, the recreation center network may be attractive to sportswear sponsors such as athletic equipment and fitness products producers. The student health center network may be sponsored by a medical or health products company to subsidize the systems within that network.

At the beginning of the school year or semester, students are given a co-branded sponsor/university card when they get their student ID card. The card may be the student ID itself in an embodiment of the invention. The student ID card may be coded for use in any university network across the country. Alternatively, students are given a co-branded bar code card and have the option of signing a waiver which means they allow their name to be used for promotional and advertising purposes by the sponsor(s).

In a further embodiment of the invention, a competition may be facilitated via one of more of the networks across a large number of universities, i.e., the "top ten." For example, an advertiser could sponsor a "Who is the Healthiest University?" contest. The contest could be based on user's measured weight and/or body fat, and/or changes in these biometric parameters over a predetermined period of time. During the contest, the sponsor or affiliate of the sponsor may provide updates regarding the progress of the participant schools. The most improved or overall fittest student body at the expiration of the contest period would be named the winner. To facilitate accurate judging, all the readings are downloaded to a main server, e.g., at a sponsor or operator. To ensure fairness and accuracy, and to avoid cheating, one or more of the security features discussed above is preferably used.

Another exemplary environment is a hospital network, i.e., a number of kiosks in one or more hospitals linked via the Internet or other network to operator and/or sponsor servers. Hospital kiosks may be provided in many areas, such as emergency rooms, gift shops, and rehabilitation departments. With respect to gift shops, the kiosk may be accessible even when the shop is closed to allow the user to view a catalog and order items during closed hours. The card reader used for identification purposes may also be used for purchasing purposes in this example.

Within the hospital network in the three systems, the sponsor can promote educational programs. In addition, many hospitals that have not-for-profit status are required to give away services to maintain the tax-exempt status. The kiosk network provides a way to give away services and to help maintain tax-exempt status and improve public relations for the hospital. In addition to the donation of services, the hospital may donate kiosk units to local worksites, fire stations, city halls, etc.

Another exemplary environment is a doctor's office network, i.e., a kiosk in one or more doctor's offices linked via the Internet or other network to operator and/or sponsor servers. In the doctors' network, patients can use their cell phone, i.e., the clear phone wireless system, to call a 1-800 number for educational information. Readings can also be downloaded and saved for the doctor's use, etc.

Yet another exemplary environment is an airline club network, i.e., a kiosk in one or more Airline Clubs linked via the Internet or other network to operator and/or sponsor servers. Preferably, the information provided by these kiosks is tailored to the location. For example, the kiosk can provide tips and information (i.e., and illustration or video of recommended exercises) useful for avoiding deep vein thrombosis—a circulatory problem often affecting air travelers. Another service is to provide weather by zip code when the user provides a destination city. The kiosk may also provide status updates for flights. Airline memberships may be advertised and purchased through the kiosk. In addition, in an embodiment of the invention the user can select items from an electronic catalog and purchase the selected items with a magnetic stripe reader located on the airline club kiosk. This aspect is also usable in any kiosk situated in a location where purchase may be desired. For example, the hospital gift shop kiosk may provide a coupon for an item and allow the user to purchase the item right at the kiosk, and/or may allow the customer to order on-line using their credit cards and have items sent to their home.

A broader example of the foregoing network is a traveler's network in which kiosks as described above may be placed in locations frequented by travelers, e.g., train stations, airports, bus stations, etc. With respect to this and other embodiments of the invention, the kiosk provides in a further enhancement the ability to communicate with the user in their preferred language. To implement this functionality, the kiosk identifies the user's original locality such as by their country code, zip code, area code, etc., and communicates in a language appropriate for that area. For example, the kiosk will communicate with American users via English text and audio (e.g., in videos). However, if the user's country code identifies them as Japanese (perhaps even traveling in another country), then the kiosk will communicate with that user via Japanese text and audio.

Yet another exemplary environment is a work site network, i.e., a kiosk in one or more work sites linked via the Internet or other network to operator and/or sponsor servers. This network would allow employees to access their readings at home and to print a history of readings. Employee readings could also be emailed with regard to health results to a user's health care provider. If the employee waives their HIPPA privacy rights to allow the employer to see the readings, then more customized services may be provided. For example, the sponsor may provide the user with information regarding products that would be of interest given the user's demographic data or health condition. Insurance companies also have interest in providing the health information kiosk free or at a discount rate in order to document healthier employee groups as a result of these services being offered. Also, individuals may be rated by the insurance company by the test results in trends, i.e., healthier individuals may receive discounts on insurance premiums, etc.

Other potential sponsors for the work site units are hospitals and drug companies. Medical departments can be given access to employee readings by group and can track trends and improvements. Work sites can also have features similar to the university networks, i.e., a "Healthiest Factory" or "Healthiest Branch" contest to encourage improvement in employee health.

Yet another exemplary environment is a health club network, i.e., a kiosk in one or more health clubs linked via the Internet or other network to operator and/or sponsor servers. This network would be attractive to insurance company sponsors. Other potential sponsors for the health club network are the same as those for the university recreation center network.

Yet another exemplary environment is a not-for-profit environment. Examples would include kiosks in religious institutions such as churches, mosques, and temples to promote religious or charitable causes, products, or activities. In an embodiment of the invention, used hearing aids and eye glasses are deposited by users in the receptacles built into the kiosk (e.g., elements 109 and 111). The received items may be donated or sold to help the disadvantaged and subsidize the kiosk. As a further embodiment of the invention in this area, local health departments may sponsor units to put into economically disadvantaged gathering places.

Food service and restaurant chains may also use the kiosks to promote their products. A large chain may comprise an entire network. Certain chains also sponsor charities that they may promote via the kiosk network.

Financial institutions may also use the kiosks to promote their products. Such institutions may desire to earn customer loyalty by providing a popular service. Sponsors may also promote and/or sell products such as credit cards, mortgages etc.

Yet another exemplary environment is a retail location environment. Sponsors may benefit by advertising the goods available in the retail location or may sell advertising time to others.

Other exemplary environments include convention centers (e.g., to provide health information), municipal buildings (City Halls, Fire Departments, etc., e.g., so customers can register for the local zoo membership, apply for car registration, etc.), government groups or centers, museums (e.g., to sell museum memberships and gift shop items), etc.

Another environment in which a kiosk system according to the invention can be beneficially employed is within a hotel or hotel chain. A user may use the kiosk via their hotel key card and/or via a computer-readable card issued for another network such as a health club or traveler's network. The hotel may benefit by advertising available hotel services such as amenities, other locations, restaurants, etc., and/or may sell advertising time to others.

Although the use of waivers has been discussed herein, in an embodiment of the invention, the customer user is able to use the kiosk (perhaps without storing readings), even if they do not consent to the waiver.

Figure 4:
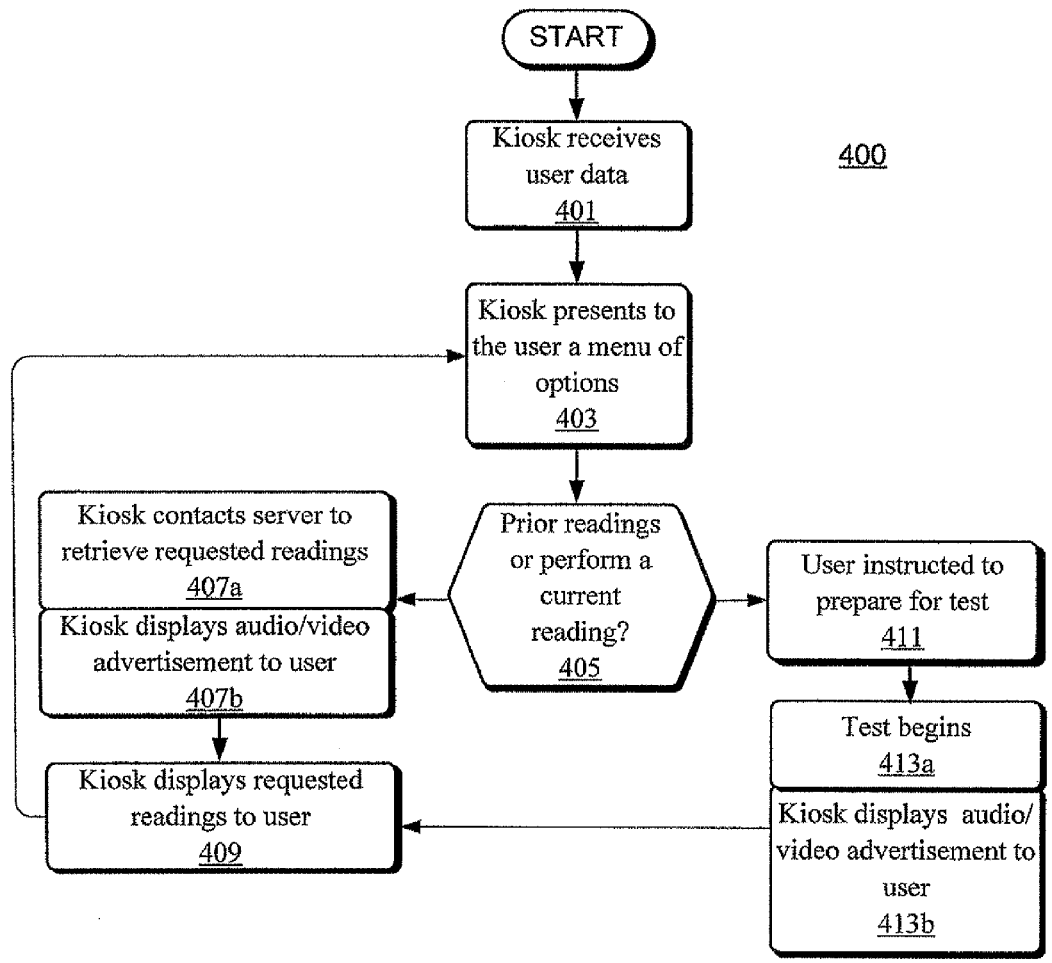
FIG. 4 is a flow chart showing a process of advertising and promotion via a kiosk according to an embodiment of the invention.

Having discussed various types of health kiosk networks and environments above, the details of certain types of exchanges facilitated by certain embodiments of the invention will now be discussed. FIG. 4 is a flow chart showing a process of advertising and promotion via a kiosk as described above. At stage 401 of the process 400, the kiosk receives user data, such as pursuant to the swipe of a user magnetic stripe card in a card reader. At stage 403, the kiosk presents to the user a menu of options. In an embodiment of the invention, the options include an option to retrieve prior readings and an option to perform a current reading.

At stage 405, it is determined whether the user wishes to retrieve prior readings or perform a current reading. If the user desires to retrieve prior readings the process flows to stage 407a, whereat the kiosk contacts a server over a network or other link to retrieve the requested readings. During this time, at stage 407b, the kiosk displays an audio/video advertisement to the user. After the advertisement has played, the kiosk presents the requested readings to the user at stage 409 and returns to stage 403.

If at stage 405 it is determined that the user wishes to perform a current reading, the process flows to stage 411, whereat the user is instructed to prepare for the test, i.e., by placing their arm in the cuff, sitting appropriately on the scale/seat, gripping a handle in a specific location etc. At stage 413a, the test begins. Concurrently in stage 413b, the kiosk presents an audio/video advertisement to the user. After the advertisement has played, the kiosk presents the requested readings to the user at stage 409 and returns to stage 403.

Figure 5:
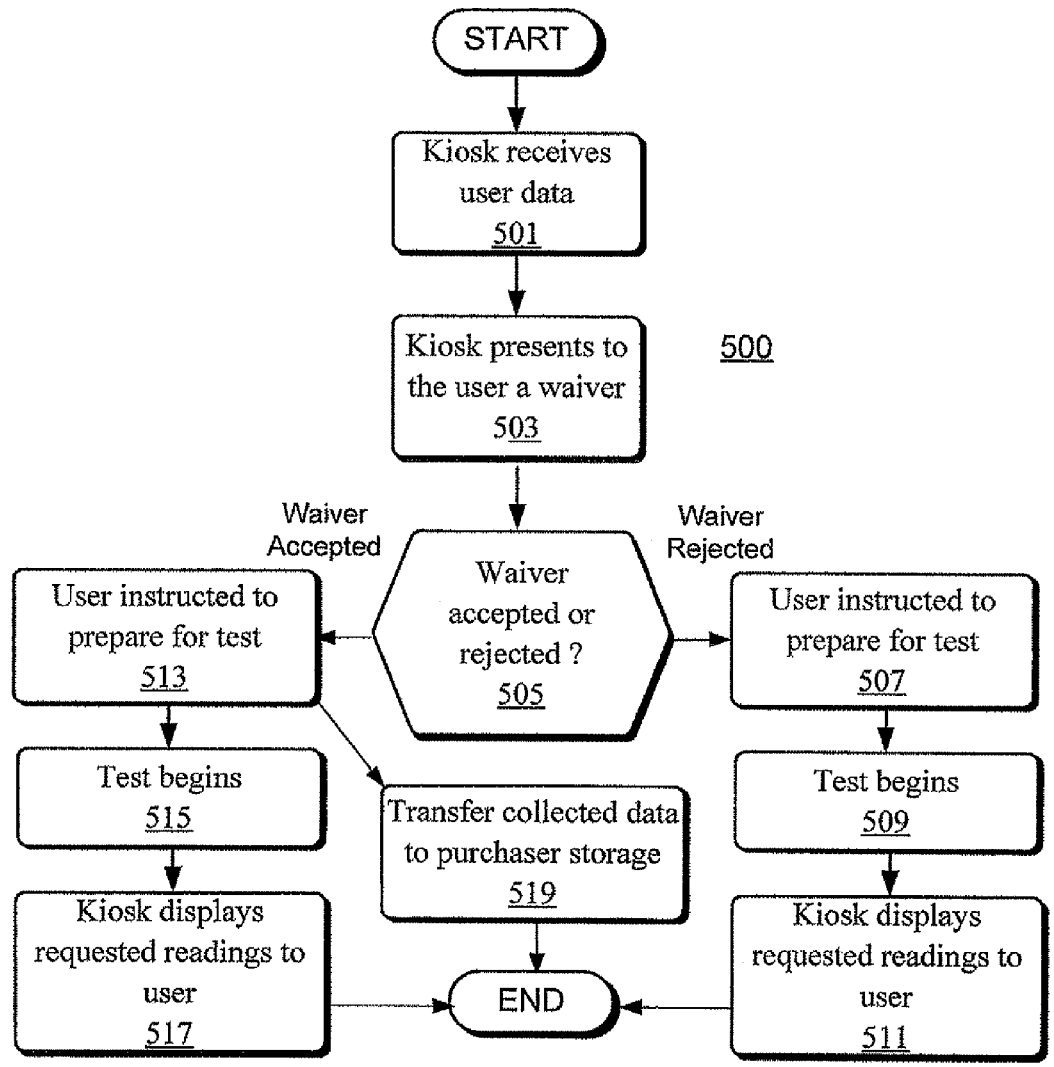
FIG. 5 is a flow chart showing a process of data collection via a kiosk according to an embodiment of the invention.

FIG. 5 is a flow chart showing a process of data collection via a kiosk as described above. At stage 501 of the process 500, the kiosk receives user data, such as pursuant to the swipe of a user magnetic stripe card in a card reader. The data may either be stored on the card or the data stored on the card may be linked to the user data by the kiosk.

At stage 503, the kiosk optionally presents a waiver to the user. This may in addition to or in lieu of a waiver signed when the user first received their card. At stage 505, it is determined whether the user has accepted or rejected the waiver. If the user has rejected the waiver, the process flows to stage 507, wherein whereat the user is instructed to prepare for the test. At stage 509, the kiosk performs the requested test and presents the results in stage 511.

If it is determined at stage 505 that the user has accepted the waiver, the process flows to stage 513, whereat the user is instructed to prepare for the test. At stage 515, the kiosk performs the requested test and presents the results in stage 517. However, in addition, from stage 515, the kiosk at stage 519 transfers the user information (i.e., name, address, demographics, etc.) to a server, where similar data from other users of the same or different kiosks is collected. Optionally, the data is temporarily stored locally and sent in batches to the server. From stage 519, the server transfers the collected data to a purchaser storage unit, e.g., another server or other computer-readable medium associated with a purchaser of the collected data.

As discussed herein, video may comprise downloaded and/or streaming video, animation, etc, and may be accompanied by sound and/or other sensory information. All references cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A network system for providing health care information to a user, the network system comprising:
   (a) a first data server; and
   (b) a biometric measurement kiosk comprising, in a single unit, a seat to receive the user, a side platform coupled to the seat to receive a user limb for biometric measurement, and a front platform coupled to the side platform, the front platform having a front platform wall and a graphical user interface associated therewith, the biometric measurement kiosk further comprising:
      (1) a measurement tool associated with the side platform that takes a measurement of a biometric parameter of a user;
      (2) an input device that receives user data from the user and associated with the user, the data comprising one or more elements selected from the group consisting of user identity data, user demographic data, and user purchasing activity data;
      (3) a network connection to convey communications between the biometric measurement kiosk and the first data server;
      (4) a kiosk processor in the biometric measurement kiosk that sends the user data to the first data server; and
      (5) a wireless communication module on the kiosk providing a bidirectional link to a cellular device carried by the user that, when active, provides communication between the kiosk and the user, wherein the wireless communication module on the kiosk calls the user's cell phone automatically, wherein the bidirectional link, once established by the wireless communication module to the user cellular device, is routed through the kiosk to a remote human recipient whereby the user and the remote recipient are placed into a call with each other through the kiosk, wherein the wireless communication module on the kiosk is triggered by a detection of a potentially dangerous state associated with the user based on the measurement.

2. The network system according to claim 1, further wherein the wireless communication module on the kiosk is further configured to be triggered by user action.

3. The network system according to claim 1, wherein the potentially dangerous state includes a blood pressure reading that indicates that the user is having, or is in danger of having, a stroke.

4. The network system according to claim 1, wherein the bidirectional link connects only to devices within the near field.

* * * * *